(12) United States Patent
Mark et al.

(10) Patent No.: US 8,206,315 B2
(45) Date of Patent: Jun. 26, 2012

(54) REAL-TIME PATHOLOGY

(75) Inventors: Joseph L. Mark, Indianapolis, IN (US); Michael E. Miller, Trafalgar, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 215 days.

(21) Appl. No.: 12/241,644

(22) Filed: Sep. 30, 2008

(65) Prior Publication Data

US 2010/0081964 A1   Apr. 1, 2010

(51) Int. Cl.
*A61B 10/00* (2006.01)
(52) U.S. Cl. ......... 600/567; 606/181
(58) Field of Classification Search ........ 600/562, 600/564, 566, 547; 606/181
See application file for complete search history.

(56) References Cited

U.S. PATENT DOCUMENTS

| | | | | |
|---|---|---|---|---|
| 4,841,984 | A * | 6/1989 | Armeniades et al. | 600/561 |
| 5,575,293 | A * | 11/1996 | Miller et al. | 600/565 |
| 5,634,464 | A * | 6/1997 | Jang et al. | 600/467 |
| 5,928,164 | A * | 7/1999 | Burbank et al. | 600/567 |
| 6,109,270 | A | 8/2000 | Mah et al. | |
| 6,142,955 | A * | 11/2000 | Farascioni et al. | 600/562 |
| 6,638,235 | B2 | 10/2003 | Miller et al. | |
| 6,718,196 | B1 | 4/2004 | Mah et al. | |
| 6,758,824 | B1 | 7/2004 | Miller et al. | |
| 7,017,416 | B1 * | 3/2006 | Liu et al. | 73/702 |
| 7,322,929 | B2 | 1/2008 | Lovoi | |
| 7,347,829 | B2 | 3/2008 | Mark et al. | |
| 2002/0026127 | A1 * | 2/2002 | Balbierz et al. | 600/567 |
| 2002/0128570 | A1 * | 9/2002 | Bowman et al. | 600/567 |
| 2006/0195126 | A1 * | 8/2006 | Snow et al. | 606/159 |
| 2007/0123815 | A1 | 5/2007 | Mark | |
| 2007/0208250 | A1 * | 9/2007 | Sullivan | 600/410 |
| 2007/0260267 | A1 | 11/2007 | Nicoson et al. | |

FOREIGN PATENT DOCUMENTS

| | | |
|---|---|---|
| DE | 102005033474 | 1/2007 |
| EP | 0 667 126 A1 | 8/1995 |
| WO | WO-2005009200 A2 | 2/2005 |
| WO | WO-2007034416 A2 | 3/2007 |
| WO | WO-2008/109760 A2 | 9/2008 |

OTHER PUBLICATIONS

"New tool speeds up cancer biopsy results", by Dr. Ronald S. Weinstein, Arizona Daily Star; May 31, 2005.
"New Microlab on Chip for Medical Imaging Biomarkers", http://www.physorg.com/news9145.html; Dec. 16, 2005.

(Continued)

*Primary Examiner* — Max Hindenburg
*Assistant Examiner* — Renee Danega
(74) *Attorney, Agent, or Firm* — Vista IP Law Group LLP

(57) ABSTRACT

A system for detecting abnormal tissue in a patient including an introducer cannula having a proximal opening and a distal opening. The system further includes a surgical instrument configured for selective insertion through the cannula. The surgical instrument further includes a tissue cutting opening positioned relative to the distal end of the introducer cannula when fully inserted through the introducer cannula. The system also includes a sensor configured to detect at least one property of the tissue of the patient. The sensor is located at a fixed distance relative to the distal end of the introducer cannula when the surgical instrument is inserted into the introducer cannula.

42 Claims, 8 Drawing Sheets

OTHER PUBLICATIONS

"High-Resolution Thin-Film Device to Sense Texture by Touch" by Dr. Ravi Saraf et al.; http://digitalcommons.unl.edu/cgi/viewcontent.cgi?artilce=1008&context=chemeng_nanotechnology; Jul. 2006.

"Impedence-based Biosensors", by X. Huang, et al.; http://www.ece.cmu.edu/~dwg/research/mrs2004.pdf.

"Microchannels, electricity aid drug discovery, early diagnosis"; http://news.uns.purdue.edu/html4Gver/2006/060621.Lu.cellchannel.html, Jun. 21, 2006.

Single-Cell Analysis: Quick and Easy Detection; by Maria Fontanazza; R&D Digest article dated Sep. 2006.

"Diangostics Devices Break Out"; by Patrick McGee, Sr. Editor, Drug Discovery & Development, Mar. 9, 2006.

International Search Report for PCT/US2009/049264 dated Sep. 10, 2009.

Article entitled "Diagnosis of non-palpable breast cancer; a review" by M.F. Ernst and J.A. Roukema; The Breast (2002 Harcourt Publishers Ltd.).

PCT International Search Report for PCT/US2011/034783 dated Jul. 18, 2011.

* cited by examiner

REAL-TIME PATHOLOGY

FIELD

This disclosure relates generally to systems and methods for pathology. More specifically, this disclosure relates to systems and methods for real-time pathology.

BACKGROUND INFORMATION

In the diagnosis and treatment of breast cancer, it is often necessary to locate, sample and remove a suspicious mass. The suspicious mass is typically discovered during a preliminary examination involving visual examination, palpitation, X-ray, MRI, ultrasound or other imaging or detection means. When this preliminary examination reveals a suspicious mass, the mass must be evaluated in order to determine whether the mass is malignant or benign. Typically, the mass is biopsied and processed by a pathology laboratory to determine whether the mass is malignant or benign. Such methods are used for early diagnosis of breast cancer, as well as other forms of cancer. The early diagnosis and subsequent treatment can prevent the spread of cancerous cells to other parts of the body and ultimately prevent fatal results.

In a breast biopsy, for example, biopsy methods may be performed by either an open procedure or a percutaneous method. The open surgical biopsy procedure first requires localization of the lesion by insertion of a wire localization while using a visualization technique, such as X-ray or ultrasound. Next, the patient is taken to a surgical room where a large incision is made in the breast, and the tissue surrounding the wire loop is removed. This procedure causes significant trauma to the breast tissue, often leaving disfiguring results and requiring considerable recovery time for the patient. This is often a deterrent to patients receiving the medical care they require. The open technique, as compared to the percutaneous method, presents increased risk of infection and bleeding at the sample site.

Percutaneous biopsies have been performed using either fine needle aspiration or core biopsy in conjunction with real-time visualization techniques, such as ultrasound, mammography (X-ray), MRI, PET, CT, terahertz technologies, etc. Fine needle aspiration involves the removal of a small number of cells using an aspiration needle. A smear of the cells is then analyzed using cytology techniques. Although fine needle aspiration is less intrusive than an open procedure, only a small amount of cells are available for analysis. In addition, this method does not provide for a pathological assessment of the tissue, which can provide a more complete assessment of the stage of the cancer, if found. In contrast, in core biopsy a larger fragment of tissue can be removed without destroying the structure of the tissue. Consequently, core biopsy samples can be analyzed using a more comprehensive histology technique, which indicates the stage of the cancer. In the case of small lesions, the entire mass may be removed using the core biopsy method. For these reasons core biopsy is often preferred, and there has been a trend towards the core biopsy method so that a more detailed picture can be constructed by pathology of the disease's progress and type.

However, each of the methods described above require that process steps be followed for the preparation of the sampled tissue by a lab (cytology or pathology) leading to significant time between the taking of a tissue sample and actually determining the tissue health due to the cytological or histological techniques employed. In the case of patient care in breast disease diagnosis and subsequent treatment, the patient has left the diagnostic location and the diagnostic room is prepared for another patient. After the initial determination is made, for example where the tissue is found to be malignant, the patient is contacted and another appointment is made for a return the diagnostic location. After the patient returns, the mass must again be located before removal in a surgical environment. Thus, even after a first sample is taken to obtain a diagnosis, a second procedure must be performed to localize the mass before the patient can be scheduled for the removal of the mass in a surgical suite. Additionally, the step of localization of the mass in this process of patient care is inaccurate. Localization devices do not always get placed in the exact location intended, or they move or shift after placement or they are not so clearly found or identified while in the surgical procedure to remove the intended mass. Even once the patient is in the surgical procedure the need for the pathology lab is still required. Often the pathology department in the hospital is called upon to "read the excised tissue" during the procedure to determine if adequate tissues have been removed to confirm in the surgeons desire to achieve clear margins during the excision of the mass. This often leads to delays during the surgical procedure since the lab must find time in their busy schedule to process the tissue and then evaluate the status of the tissue all while the patient is lying in the operating room.

In light of the foregoing disadvantages, a need remains for a diagnostic system that improves the response time for diagnosis and treatment of suspicious tissue. Moreover, where desired, the diagnostic and treatment system may also provide for removal of the tissue at a particular location where a sample is taken. It is further desired that the system be able to detect suspicious tissue in less time than standard techniques. Moreover, it is preferred that the system detect suspicious tissue in real-time or near-real-time. A need also remains for a diagnostic system that is compatible with multiple imaging modalities including, but not limited to MRI.

BRIEF SUMMARY

A system for detecting abnormal tissue in a patient that may include an introducer cannula having a proximal opening and a distal opening. The system may further include a surgical instrument configured for selective insertion through the cannula. The surgical instrument has a tissue cutting opening positioned relative to the distal end of the introducer cannula when fully inserted through the introducer cannula. The system also includes a sensor configured to detect at least one property of the tissue of the patient. The sensor is located at a fixed distance relative to the distal end of the introducer cannula when the surgical instrument is inserted into the introducer cannula.

Also disclosed is a system for detecting normal or abnormal tissue in a patient. The system may include an introducer cannula having a proximal opening and a distal opening. A tissue resection device is configured for insertion through the cannula, the tissue resection device further including a tissue cutting opening positioned relative to the distal opening of the introducer cannula. Also, a sensor configured to detect abnormal tissue of the patient relative to the distal opening of the introducer cannula.

Additionally, a system for detecting normal or abnormal tissue in a patient is disclosed. The system may include an introducer cannula having a proximal opening and a distal opening. The system also includes a sensor configured to detect at least one property of the tissue of the patient. A tissue resection device is configured for insertion through the cannula. The tissue resection device is also configured to sever tissue from the patient and convey the severed tissue to the sensor.

BRIEF DESCRIPTION OF THE DRAWINGS

Features and advantages of the disclosure will be apparent from the following detailed description and the appended claims, taken in conjunction with the accompanying drawings, in which:

DETAILED DESCRIPTION OF THE EMBODIMENTS

Figure 1:
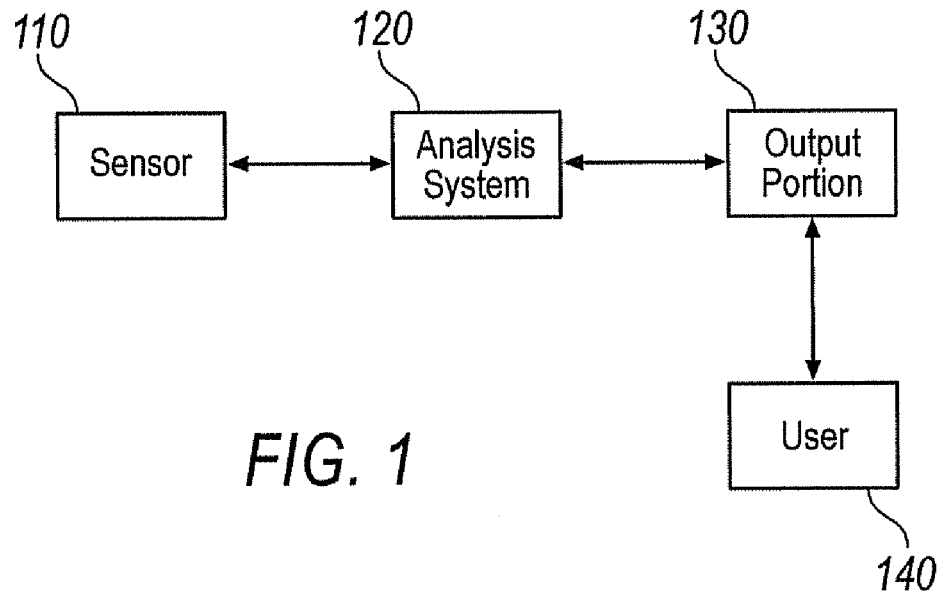
FIG. 1 is an example functional diagram of a real-time pathology system.

Referring to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the disclosure to the precise form and configuration shown in the drawings and disclosed in the following detailed description.

Overview

The systems and methods discussed herein generally refer to in-vivo sensing of tissue of a patient to detect predetermined tissue conditions (e.g., the detection of cancer or otherwise abnormal tissue). The in-vivo system does not require removal of tissue off-site for testing or removal of tissue for local testing by a separate analyzer (e.g., a surgical pathologist reviewing a slide). The systems described herein allow the user to insert a medical instrument into a patient, resect a portion of tissue, and perform an analysis in real-time. In some embodiments, the tissue need not even be resected in which case the user may insert a probe into a cavity that may have already been resected in order to test whether an appropriate margin has been created.

The real-time aspect of the systems and methods described herein do not refer to perfectly instantaneous testing, but rather are considered to be tested and analyzed quickly during the medical procedure undertaken such that the user (and a patient) is not waiting a long period of time for results. In this way, when a user resects a portion of tissue and the device makes a determination during the procedure, such a system is considered real-time because the user may continue to resect tissue and repeat the testing procedure without a burdensome delay.

In one example, real-time pathology may be performed during a biopsy procedure (e.g., a core sample or needle biopsy). When the user inserts a needle into a patient and resects a tissue sample the real-time pathology system performs a pathology test. The user is then presented with a pathology report, the results of the pathology test being reported to the user. Such a system does not require removal of the tissue sample from the biopsy device and subsequent pathology testing. The procedure may then be repeated multiple times if the user desires to sample other regions of the patient.

In another example, real-time pathology may be performed using a bulk surgical device, such as a breast biopsy device. Examples of such biopsy devices are described in co-pending U.S. patent application Ser. No. 11/865,092, entitled "SURGICAL DEVICE," filed on Oct. 1, 2007 and commonly assigned U.S. Pat. Nos. 6,758,824 and 6,638,235, both entitled "BIOPSY APPARATUS," the contents of which are incorporated by reference in their entirety. During a bulk resection procedure, the user may remove tissue at a suspected cancer site. When the user has resected the suspect tissue, the margins may be sampled to determine whether enough tissue has been removed around the suspect region. The real-time pathology system may be built into the surgical device (e.g., at the sampling region or along the tissue evacuation path). Thus, the user may sample the margin region and perform the real-time pathology testing without removing the surgical device. When the results of the real-time pathology test are presented to the user, the user may determine that the margin is adequate (e.g., no cancer cells are detected) or that more resection is needed (e.g., suspicious cells are detected).

In one example, a tissue removal or resection device used for breast biopsy is attached to a stereotactic table for positioning. A patient's target area for tissue removal is immobilized (e.g., a breast) in relation to the tissue removal device. The stereotactic table allows visualization of the target area and location of fiducia that allow for precise movement and positioning of the tissue removal device. In many cases, the tissue removal device is a surgical device, such as is described in detail below and in the drawings. When the surgical device is installed with a positioning system, movements of the positioning system allow for the precise removal of tissue samples. Moreover, a surgeon may use one or many visualization systems (i.e., imaging modalities) to further identify a target area and then precisely position the surgical device to remove tissue at the target area. The imaging modalities include, for example, MRI, PET, CT, ultrasound, terahertz technologies, etc. The location of the target area is determined and the position is recorded for manual or automatic movement of the positioning system and the surgical device.

Once the surgical device is positioned, an introducer cannula may be inserted within the patient close to the target site. A real-time pathology system may be employed separately or in addition to a visualization system to further identify and locate the suspicious tissue. Where visualization will allow the user to locate a specific site identified by, for example, a site marker or indicia, the real-time pathology system allows the user to test the tissue itself to determine an appropriate location or locations for tissue resection. Moreover, the real-time pathology system may be used to determine the boundaries of the tissue to be resected, and whether all of the tissue has been removed after bulk resection. Further, before, during, or after abnormal tissue is identified and/or removed, one or more treatments may also be introduced at the target site. Such treatments include brachytherapy and other adjuvant treatments (such as, ablating tissue, heating tissue, freezing tissue, applying chemicals to tissue, external beam HIFU therapy, interstitial HIFU therapy, electroporation therapy, ultrasonicporation therapy, interstitial microwave therapy, etc.).

FIG. 1 is an example functional diagram of an exemplary real-time pathology system 100. System 100 includes a sensor 110, an analysis system 120, an output portion 130, and a user 140. Sensor 110 may be configured as at least one mechanism used to detect predetermined tissue conditions such as cancerous cells, abnormal cells, and/or pH (i.e., acid, neutral, alkaline), or other measurable parameters. Moreover, analysis system 120 may also provide information using inferences developed from models, such as the abnormality of cells based on a statistical model of the measured parameters. Alternatively, sensor 110 may provide analysis system 120 with a digital and/or analog signal(s) that is interpreted for its presence or with respect to a threshold to determine whether the sensed tissue is abnormal.

In general, real-time pathology system 100 is used to detect normal or cancerous tissue or otherwise abnormal tissue. The results of real-time pathology system 100 are then provided to the user temporally very close to when detection is performed, or continuously, depending upon the configuration and mode of operation selected for real-time pathology system 100.

Alternatively, sensor 110 may include a multitude of sensors used to independently or together determine whether a predetermined pathologic condition is present at the tissue being tested. Generally, sensor 110 may include optical components including a light source, a lens, and/or a light detector which may be selectively sensitive to particular wavelengths or which may be sensitive to a wide range of frequencies to be further processed. Sensor 110 may be passive, which generally includes only a detector. Alternatively, sensor 110 may be an active sensor which may include a light source that provides a single frequency of light or a wide frequency range. The light source may also be tunable to provide different frequencies at different times or a multitude of selected frequencies at the same time.

Sensor 110, when configured as an optical sensor component, may include an array microscope, which includes multiple small lenses in combination with a mega-pixel camera. An example of such a microscope is described in "New tool speeds up cancer biopsy results", by Dr. Ronald S. Weinstein, which can be found at "http://www.azstamet.com/sn/health/77532.php", the contents of which are included in their entirety herein. The microscope is typically a passive device that may have increased sensitivity for predetermined wavelengths that are characteristic of diseased or healthy tissue. The appearance of these wavelengths may be further enhanced with a marker system that may include dyes or other compounds that seek out diseased tissue to mark them. Other microscope systems may include optical systems that look for cellular structure issues. The analysis system may be within the sensor or outside the device in, for example, a control console. Active optical sensors may include emissive components that illuminate suspect tissue with a particular wavelength (or wavelengths) or a laser source. The optical sensors may then measure the returning or reflected light and make a determination as to cellular health. For example, the optical sensors may read the reflected wavelength or the phase-shift of the light.

In another example, sensor 110 may require the addition of a marker to identify suspect cells. One example includes the use of a marker in conjunction with positron emission tomography (PET). Sensor 110 may then be configured as a microfluidic chip that produces markers while in the patient. See also the article "New Microlab on Chip for Medical Imaging Biomarkers" which can be found at "http://www.physorg.com/news9145.html", the contents of which are included in their entirety herein. Alternatively, another example includes using dyes to identify suspect cells as is described in German Patent Publication No. DE 10200 50 33474 entitled "Investigating tissue samples, especially for cancer diagnosis, comprises assigning fluorescence-labeled samples to positional coordinates, irradiating the samples and determining the fluorescence intensity", the contents of which are included in their entirety herein.

Sensor 110 may also include chemical sensors. For example, sensor 110 may be configured to detect a predetermined chemical marker from the resected tissue. Alternatively, sensor 110 may include a reagent that reacts with the resected tissue to determine the presence of a predetermined chemical, protein, or other indicator. Moreover, the tissue may have been treated with a marker agent to enhance or identify suspect tissue. Sensor 110 may also be a single cell or an array of distinct polynulceotides, oligonucleotides, polypeptides, or oligopeptides synthesized on a substrate which may also include electronic sensors to detect and transmit a reaction therein. An example is an AmpliChip® module manufactured by Roche Diagnostics which may be used in vitro, and adapted for in vivo use. As discussed herein, sensor 110 may be used generally in vivo or in situ at the tissue resection site. Alternatively, as discussed herein sensor 110 may be used in vitro but still as accompanying a surgical device (discussed below when sensor 110 is in the fluid path in FIG. 4F).

In another example, sensor 110 may be configured to detect the surface geometry of a cell. For example, tactile sensors may be used to determine the surface geometry and density of the tissue, similar to human palpation. An example is shown in "High-Resolution Thin-Film Device to Sense Texture by Touch" by Dr. Ravi Saraf et al., which may be found at "http://digitalcommons.unl.edu/cgi/viewcontent.cgi?article=1008&context=chemeng_nanotechnology", the contents of which are included in their entirety herein.

In another example, sensor 110 may be configured as an impedance sensor to determine the resistivity or conductivity of adjacent tissue. The sensor may include electrodes and may be driven by a signal configured to detect the impedance of living tissue. The signals may then be sent to a processor for further analysis. Typically, resistivity or conductivity is measured by sensor 110 and a model is used by a processor to determine the difference between healthy tissue and suspicious tissue based on the impedance readings. An example of such sensors is described in "Impedance-based Biosensors", which can be found at "http://www.ece.cmu.edu/~dwg/research/mrs2004.pdf", the contents of which are included in their entirety herein.

Sensor 110 may also be configured to modify a cell from the resected tissue in order to add materials to the cell or to provide access direct access for intercellular testing. For example, sensor 110 may include elements that perform electroporation in order to open a portion of the cell wall without destroying the cell (e.g., through cutting or bursting). In this example, electroporation is used to sense internal chemicals of the cell in a single-cell analysis procedure. Additionally, certain electroporation processes may be used to determine cancerous or cells that contain precursors to cancer. An example of which is describe in "Microchannels, electricity aid drug discovery, early diagnosis" which can be found at "http://news.uns.purdue.edu/html4Gver/2006/060621.Lu-.cellchannel.html", the contents of which are included in their entirety herein.

Using electroporation, an undamaged cell may be opened and is considered uncontaminated. Electroporation may be used on sensor 110 having at least two probes to provide an electric field which opens the cell wall. The open cell wall allows intracellular material to be brought to the sensor for further analysis. In another example, the electroporation allows for sensors to be inserted into the cell (e.g., as between the electric field probes). The probes may be configured as micro-spikes that invade the cell wall without breakage of the cell wall. In this way, sensor 110 is provided access to the inside of the cell without breakage of the cell or contamination of the intracellular material.

Analysis system 120 may include methods and processes for determining suspect tissue from healthy tissue, and formatting the determination into an output for the user. Moreover, analysis system 120 may also include aspects of sensor fusion where more than one method of detection is used for sensor 110. For example, sensor fusion may be utilized when an active optical sensor and a pH sensor are used, the combination of outputs from the active optical sensor and pH sensor being analyzed together to determine the possible abnormality of the tissue. Output portion 130 may include indicators, displays, sound-devices, and other systems to provide information to user 140.

Figure 2:
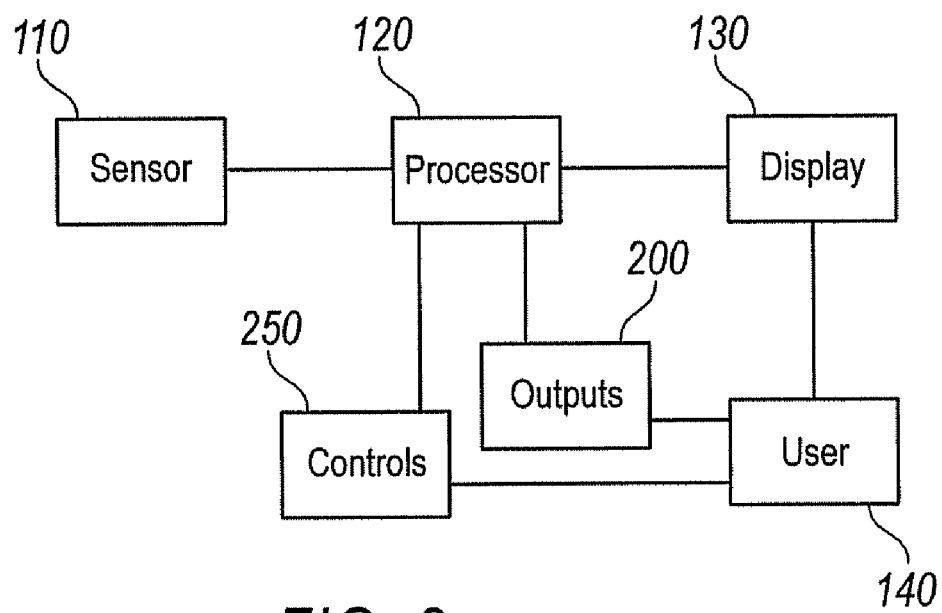
FIG. 2 is an example system diagram for the real-time pathology system shown in FIG. 1.

FIG. 2 is an example system diagram 200 for real-time pathology system 100 (shown in FIG. 1). System diagram 200 includes sensor 110, a processor 220, a display 230, user 140, controls 250, and outputs 280. User 140 may be a surgeon or technician who operates real-time pathology system 100. However, user 140 may also be considered another mechanism that is linked to real-time pathology system 100.

Sensor 110, also discussed above, may be a single sensor or a plurality of sensors. The location of sensor 110 may be at various predetermined locations on a surgical instrument as discussed below with regard to FIGS. 4A-4H.

Processor 220 is located within or connected to a surgical device (e.g., an obturator, stylet, bulk resection device, biopsy device, etc.) or external to the surgical device (e.g., at a control console, etc.). Processor 220 may be a general microprocessor and/or may include signal processing functions to filter and analyze signals provided by sensor 110.

The determination of whether tissue is abnormal may be performed by a number of methods, including a digital reading from sensor 110, using a combination of signals from multiple sensors 110, and using a model of expected "normal" tissue in comparison to a model of expected "abnormal" tissue, which may include cancer.

The models may be empirically based or may use statistical data to detect a wide variety of tissue abnormalities. Moreover, processor 220 may be configured or selectively configurable for the type of tissue that real-time pathology system 100 is being used for. In an example, processor 220 may be configured to detect abnormal tissue within a patient's breast. In another example, processor 220 may be configured to detect abnormal tissue within a patient's brain. Although the abnormal tissues in the breast and brain may be similar in origin (e.g., cancerous) they may also present different characteristics (e.g., cell-types, chemical markers, impedances, etc.) to sensor 110. Thus, processor 220 may further improve accuracy in determining an abnormality by taking into account information about where the suspect tissue is located in the patient's body (e.g., brain or breast).

Display 230 may include an indication of the current "mode" the system is in, whether resection is in progress, and an indication of the health or abnormality of the tissue. Additionally, display 230 need not be at a single location, but may generally be indicators that may appear adjacent to or within real-time pathology system 100. For example, a lighted indicator (e.g., a red light and/or a green light) may be present at the surgical instrument where sensor 110 is attached. Alternatively, a light and/or sounding device may be present at a control panel to display to the user the status or findings of real-time pathology system 100. For example, when real-time pathology system 100 encounters abnormal tissue, a red light may appear as well as a sound that indicates abnormal tissue. This alerts user 140 and allows user 140 the option to resect the abnormal tissue (and possibly the surrounding tissue).

Controls 250 may include a single input or any number of inputs that allow user 140 to determine the functionality of real-time pathology system 100. For example, in a manually controlled system, the user may push a button to begin the analysis process. This may be done when tissue has been bulk resected and a final sample near the margin is to be tested. After resecting from the margin region, the user may activate the analysis functions to test the margin. In another example, the user may wish to continuously test samples taken during resection. In this case, the continuous analysis selection may be made and the system will continuously sample at a predetermined interval. Thus, the user may begin resecting at a location that is known to include suspect tissue and the user may continue to resect tissue until real-time pathology system 100 indicates the tissue is "clear" (e.g., no suspect tissue was identified for a predetermined number or volume of samples).

Controls 250 may also be used to control the device that real-time pathology system 100 is working with, for example a breast-biopsy device. In this case, controls 250 may operate to control whether the biopsy device is in biopsy mode (e.g., resecting samples), lavage mode (e.g., for washing out a biopsy cavity), treatment mode (e.g., used to deliver therapeutics to the biopsy cavity), or pathology mode (e.g., single-sample real-time testing of tissue).

Another example of controls 250 may include the user defining the type of testing to be performed, for example where sensor 110 includes the capability for multiple types of testing. For example, the user may select active optical testing after a dye has been added at the target site. Such a user selection may also be used when the user transitions from debulking to margin testing. Here, the user may debulk a portion of tissue and when the user determines that the debulking is complete, the margins may be examined. The user may then introduce a marking agent that prefers suspicious cells. The marking agent is then absorbed by any suspicious cells (e.g., cancer cells) and controls 250 then controls real-time pathology system 100 to test for the presence of the marking agent in cells. When then marking agent is found, additional tissue resection is performed at the target site. This method of selective testing allows the user to resect tissue and to test the tissue in real-time without the need for removal of the surgical device or repositioning of the surgical device. In this way, the user is able to determine if suspicious tissue remains and to perform additional resection at the same position that the prior sample was removed from. Thus, the chance of continued resection at an incorrect location is reduced. Moreover, the user may perform resection at multiple areas and improve the confidence that the margin is indeed "clear".

The appearance of these wavelengths may be further enhanced with a marker system that may include dyes or other compounds that seek out diseased tissue to mark them. Other microscope systems may include optical systems that look for cellular structure issues, the analysis system may be within the sensor or outside the device in, for example, a control console. Active optical methods (e.g., emission of light) may be used to determine the health of the adjacent tissues and thus, assist user 140 to determine whether the margin is clear.

The user may be apprised of the results of real-time pathology system 100 by visual or auditory indications at outputs 280. For example, when performing margin testing, the system may indicate a clear margin when user 140 takes samples at multiple positions and no suspect tissue is found. Other indications provided by outputs 280 may include audible signals to user 140 that indicate the presence of suspicious tissue while operating in continuous-sampling mode (explained below in detail with respect to FIG. 7).

Figure 3A:
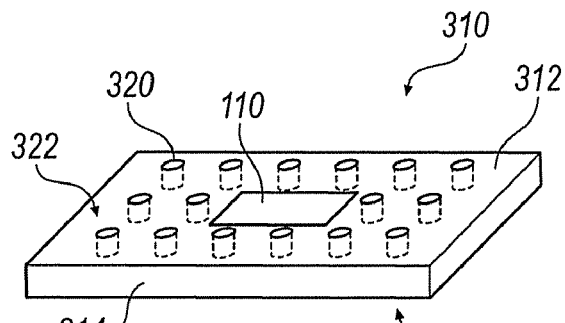
FIG. 3A is a perspective view of a sensing unit and a sensor for use with the real-time pathology system shown in FIG. 1.

FIG. 3A is a perspective view of a sensing unit 310, including sensor 110, mounted with a vacuum surface 312 to assist in drawing tissue to sensor 110 and steadying the tissue in contact with sensor 110. A substrate 314 includes a plurality of vacuum holes 320 that allow a vacuum to develop on a tissue side 322, the vacuum being supplied by a vacuum side 324. Vacuum side 324 may be attached to a vacuum source and vacuum holes 320 pull the tissue toward sensor 110 and hold the tissue in place while sampling occurs. The vacuum developed at vacuum side 324 may be separately operated similarly to a general aspiration line.

As discussed herein, sensing unit 310 may include sensor 110 as an integral component or an additional component. Moreover, sensor 110 may not include a sensing unit 310 (e.g., having features for tissue holding) but may be separately mounted to a surgical device (e.g., a stylet or an obturator).

Figure 3B:
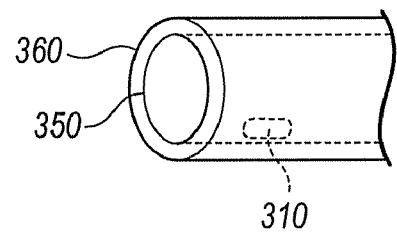
FIG. 3B is perspective view of a portion of a tissue resection device with the sensing unit of FIG. 3A positioned therein.

In one example, sensing unit 310 may be configured as part of an inner cannula of a "cannula-within-a-cannula" surgical resection device. For example, as shown in FIG. 3B, sensing unit 310 is part of an inner cannula 350 which is slidably disposed within an outer cannula 360. Substrate 314 includes inner cannula 350 and a vacuum may be developed between outer cannula 360 and inner cannula 350 to draw the tissue to vacuum holes 320 and sensor 110. Examples of such cannula-within-a-cannula surgical devices are described in commonly assigned U.S. Pat. Nos. 6,758,824 and 6,638,235, both entitled "BIOPSY APPARATUS", the contents of which are included in their entirety herein.

Figure 4A:
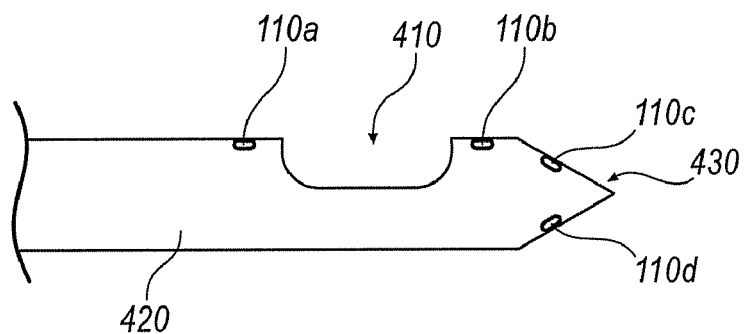
FIG. 4A is a cross-sectional view of a tissue resection device with sensors located adjacent a sampling aperture.

FIG. 4A is a cross-sectional view of sensors 110 located adjacent a sampling aperture 410 of an outer sheath 420 of a resection device. Each sensor 110A, 110B, 110C, 110D is located to further allow user 140 to guide the instrument and determine the location of suspicious tissue. In an example of a guiding operation, a piercing tip 430 provides low effort insertion of outer sheath 420 into the patient. Piercing tip 430 may be configured, for example, as a Trocar tip. Sensors 110C, 110D are positioned near piercing tip 430 (or in this case are shown as part of piercing tip 430) and provide an indication as to the potential abnormality of the tissue as outer sheath 420 is inserted into the patient. Real-time pathology system 100 may be configured to receive and process signals from sensors 110C, 110D during the insertion step of a surgical procedure to more precisely assist in the positioning of outer sheath 420 for a resection procedure.

In another example, while tissue resection is being performed, sensors 110A, 110B are located adjacent sampling aperture 410 and provide user 140 with an indication as to the health or abnormality of the immediately adjacent tissue within the patient. Thus, resection may be continued until sensors 110A, 110B do not indicate abnormal tissue. Moreover, because sensors 110A, 110B are located near sampling aperture 410, the tissue resection system may be rotated and the indications from sensors 110A, 110B also indicate the health of the adjacent tissue during rotation. For example, when sampling aperture 410 is rotated sensors 110A, 110B also indicate the health or abnormality of the tissue relative to sampling aperture 410.

Figure 4B:
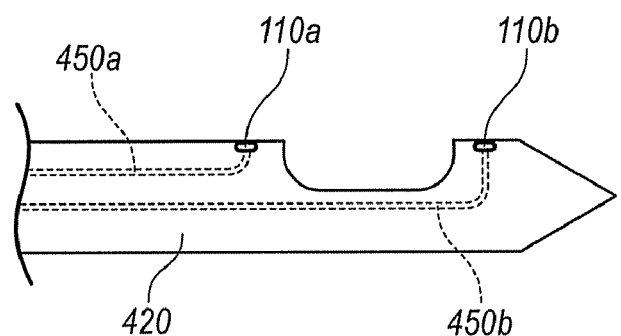
FIG. 4B is an elevational view of signal lines that electrically connect sensors to a processor.

FIG. 4B is a perspective view of signal lines 450A, 450B that electrically connect sensors 110A, 110B to processor 220 (shown in FIG. 2). As shown, signal lines 450A, 450B are disposed on the outside of outer sheath 420. In an example, signal lines 450A, 450B may be conventional wires that are glued or otherwise affixed to outer sheath 420. Other examples may include flat-flex-cable (FFC) that is affixed to outer sheath 420. In another example, signal lines 450A, 450B may be metallized (e.g., by sputtering) regions that are patterned (e.g., by etching). Such metallization may be performed on, for example, a stainless steel outer sheath 420 that has been coated, or a plastic sheath.

Figure 4C:
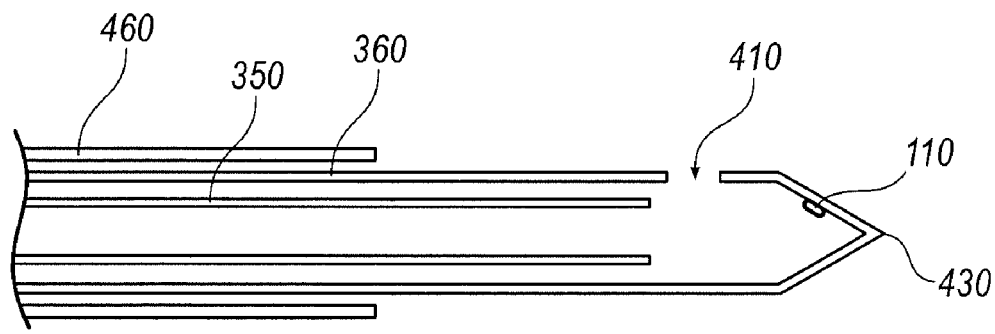
FIG. 4C is a cross-sectional view of a resection device having a sensor located adjacent a sampling aperture.
Figure 4D:
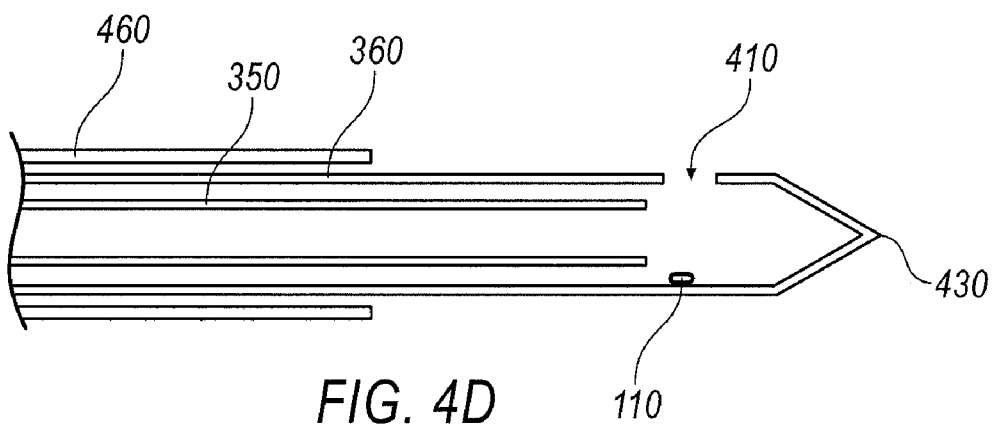
FIG. 4D is a perspective view of a resection device having a sensor located adjacent a piercing tip of a stylet.

FIG. 4C is a cross-sectional view of sensor 110 located near a sampling aperture 410 of an outer cannula 360. An introducer cannula 460 may be configured differently than outer sheath 420 (of FIG. 4B) in that introducer cannula 460 typically has an open end. In this example, sensor 110 is positioned on the inside of outer cannula 360 near sampling aperture 410 so that when tissue is prolapsed through sampling aperture 410, it is exposed to sensor 110. User 140 may then decide to resect the prolapsed tissue or to use sensor 110 to probe the surrounding tissue to determine the presence of suspicious tissue (if any). In this example, signal lines 450A, 450B (see FIG. 4B) that electrically connect sensor 110 with processor 220 (see FIG. 2) may be positioned on the inside of outer cannula 360 or and may be routed between inner cannula 350 and outer cannula 360 to processor 220. FIG. 4D is a cross-sectional view of sensor 110 located on an inner surface of outer cannula 360 generally opposite sampling aperture 410.

Figure 4E:
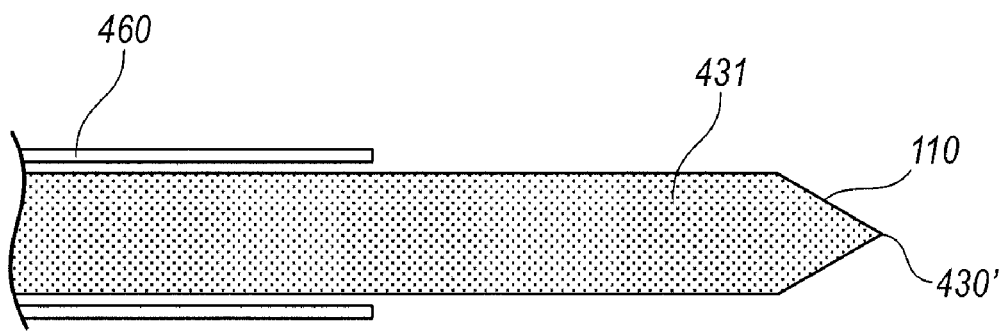
FIG. 4E is a perspective view of a stylet having a sensor located adjacent an integral piercing tip.

FIG. 4E is a perspective view of sensor 110 located near a piercing tip 430' of a stylet 431. In this example, stylet 431 does not include resection capability, but is used to pierce tissue for the insertion of introducer cannula 460. Sensor 110 is located on piercing tip 430' of stylet 431 to allow for indication of abnormal tissue during the insertion procedure. Sensor 110 may be used to guide the surgical device to the target region. When outer introducer cannula 460 is first positioned, piercing tip 430' will further pierce tissue as inserted. User 140 may then watch or listen for an indication of abnormal tissue to indicate that the target site is being neared, or that the resection procedure should begin at the present location. When sensor 110 detects abnormal tissue, user 140 may stop insertion of stylet 431 (and introducer cannula 460) so that the resection device may be inserted to remove tissue. Once tissue removal is performed, user 140 may reinsert stylet 431 and further probe the patient for addition abnormal tissue. Sensor 110 may use signal lines 450A, 450B (see FIG. 4B) as wires that are affixed to the outside of stylet 431 or may be routed through a channel with stylet 431 to processor 220.

Figure 4F:
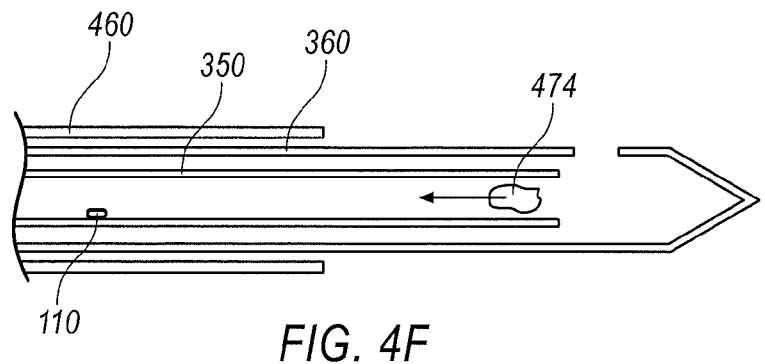
FIG. 4F is a cross-sectional view of a sensor located in a fluid path of a resection device.
Figure 4G:
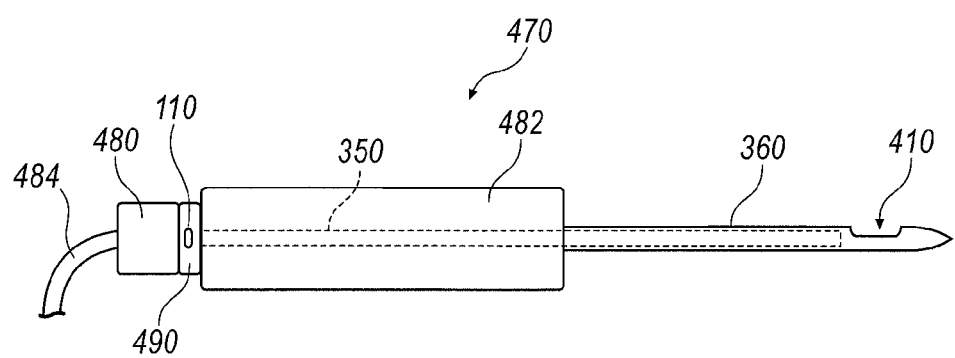
FIG. 4G is a cross-sectional view of a sensor located as an attachment to a resection device, the attachment being located between the resection device and a tissue collection canister.

FIG. 4F is a cross-sectional view of sensor 110 located in a fluid path of a resection device (see also FIG. 4G). Sensor 110 is located within inner cannula 350 of the surgical device and generally describes how sensor 110 may be placed within the fluid path, or tissue path, of a resection device to provide real-time pathology results to user 140. This is in comparison to sensor 110 as placed on piercing tip 430 (shown in FIG. 4E). FIG. 4F operates to analyze severed tissue or fluids rather than external tissue that remains (as attached to the patient). When a vacuum is applied, a portion of resected tissue 474 moves through inner cannula 350 to sensor 110. The vacuum pulls resected tissue 474 to sensor 110 and allows sensor 110 to perform the pathology sensing.

FIG. 4G is a cross-sectional view of sensor 110 located as an attachment to a resection device 470, the attachment being located between resection device 470 and a suitable tissue collection filter 480. Resection device 470 includes a handpiece 482, outer cannula 360, sampling aperture 410, inner cannula 350, and tissue collection filter 480. Inner cannula 350 severs tissue that is prolapsed into sampling aperture 410. A vacuum line 484 draws the severed tissue through inner cannula and into a real-time pathology module 490. Real-time pathology module 490 includes sensor 110 and is configured for placement between handpiece 482 and collection filter 480. Real-time pathology module 490 may include multiple sensors 110, as well as other apparatuses for holding tissue (see FIG. 3). Collection filter 480 may be used to preserve any abnormal samples for later pathology testing, if desired.

Real-time pathology module 490 may be configured for twist-on engagement with handpiece 482 allowing for its use with a variety of resection devices. The modular system for real-time pathology module 490 also allows the system to be used with legacy resection devices that use external tissue collection apparatuses. For example, one such tissue collection apparatus is described in commonly assigned U.S. Pat. No. 5,575,293 entitled "APPARATUS FOR COLLECTING AND STAGING TISSUE", the contents of which are included in its entirety herein. While such a tissue collection apparatus effectively retains tissue that is being resected to permit inspection, it may also permit staging of tissue to facilitate analysis of tissue by a pathologist.

Figure 4H:
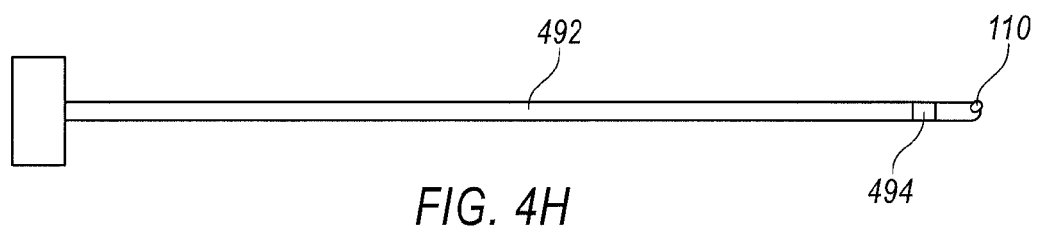
FIG. 4H is a side view showing sensor located on an obturator.
Figure 4:
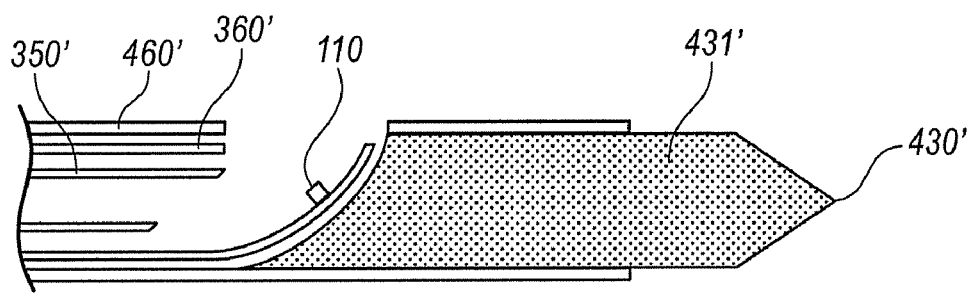
FIG. 4I is a cross-sectional view of a portion of a resection device positioned in an introducer.
FIG. 4J is a cross-sectional view of a portion of a resection device positioned in an alternative embodiment of an introducer.

FIG. 4H is a side view showing sensor 110 placed on an obturator 492. Obturator 492 may be a localizing obturator that includes a targeting ring 494 (e.g., a ring including a substance which produces an artifact in the desired imaging modality) which allows user 140 to determine the location of obturator 492 using an imaging modality (e.g., MRI and/or ultrasound). Sensor 110 may be placed near targeting ring 494 so that user 140 may locate suspicious tissue in an image. After determining the location of suspicious tissue, user 140 may place a surgical site marker in the position of interest, bulk resect tissue, and/or take a biopsy for further analysis. Typically, obturator 492 may be inserted through introducer cannula 460 (see FIG. 4D) into the patient. Alternatively, obturator 492 may not include targeting ring 494 and be used primarily for real-time analysis at select locations.

Generally, targeting ring 494 may be used for visualizing where the real-time pathology is being performed relative to, for example, the outer walls of the resection cavity which may be useful in determining where margin tests are being performed. Examples of localizing obturators may be found in co-pending U.S. application Ser. No. 11/516,277, entitled "LOCALIZNG OBTURATOR," filed on Sep. 6, 2006 and commonly assigned U.S. Pat. No. 7,347,829, entitled "INTRODUCTION SYSTEM FOR MINIMALLY INVASIVE SURGICAL SYSTEMS, the contents of which are included in their entirety herein.

Figure 4J:
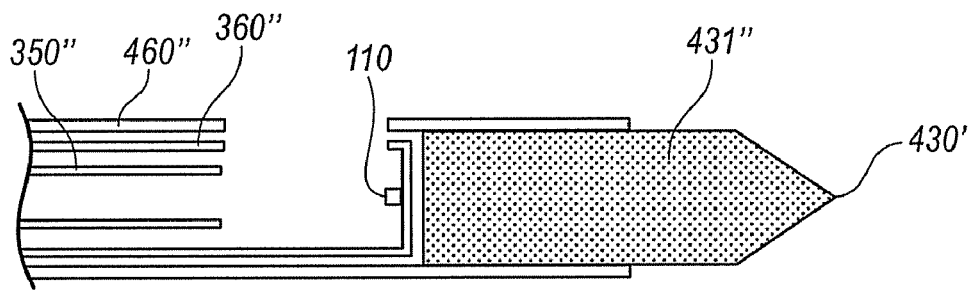

FIGS. 4I and 4J are side views of alternative embodiments of an introducer cannula 460', 460". Referring first to FIG. 4I, introducer cannula 460' is generally hollow, but is further provided with an aperture formed in a sidewall. Distal of the aperture, is a stylet 431' that includes a piercing tip 430'. Stylet 431' is fixedly secured to a distal end of introducer cannula 460'. A portion of stylet 431' that is adjacent to the aperture is formed as a ramp leading to the aperture.

FIG. 4I also illustrates an outer cannula 360'. The outer cannula 360' includes a generally curved distal end that terminates in a sampling aperture. Sensor 110 may be positioned on a portion of outer cannula 360.' An inner cannula 350' may also be seen in FIG. 4I. In this embodiment, a distal end of the inner cannula is configured in an angled configuration so as to permit complete severing of tissue as tissue is drawn into the sampling aperture of the outer cannula 360'. Further, as the distal end of the inner cannula 350' moves toward the distal end of the outer cannula 360', tissue will be forced into contact with sensor 110.

The embodiment shown in FIG. 4J is similar to that of FIG. 4I in that a stylet 431" having a piercing tip 430' is provided that is fixedly secured to a distal end of introducer cannula 460". However, a proximal end of the stylet 431" is not formed as a ramp and terminates adjacent an aperture formed in the sidewall of the introducer cannula 460". Further, outer cannula 360" is formed as having a blunt shaped distal end that is positioned adjacent a sampling aperture formed in the outer cannula 360" sidewall. And inner cannula 350" includes an open distal end that is not angled like that shown in FIG. 4I. Sensor 110 is positioned on the wall of the outer cannula 360" that forms the blunt and closed distal end. As inner cannula 350" moves across the sampling aperture in the outer cannula 360" while tissue is draw therein, inner cannula 350" will push tissue against sensor 110 as it is cutting the tissue.

Figure 5A:
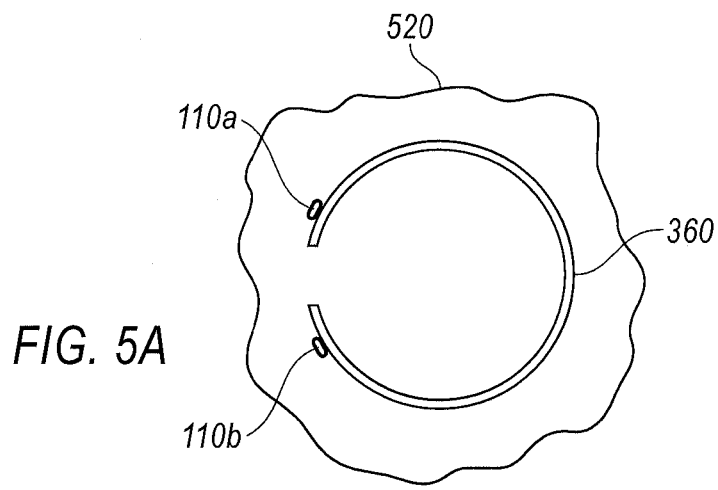
FIG. 5A illustrates a cross-sectional view of a resected cavity before a margin test is performed for the real-time pathology system of FIG. 1.

FIG. 5A shows a cross-sectional view of a resected cavity before a margin test is performed for real-time pathology system 100. In FIG. 5A, tissue has been resected and a remaining cavity wall 520 is shown positioned away from outer cannula 360 and sensors 110A, 110B. The tissue was resected through sampling aperture 410 until a volume of tissue was removed or until real-time pathology system 100 indicated no abnormal tissue present.

Figure 5B:
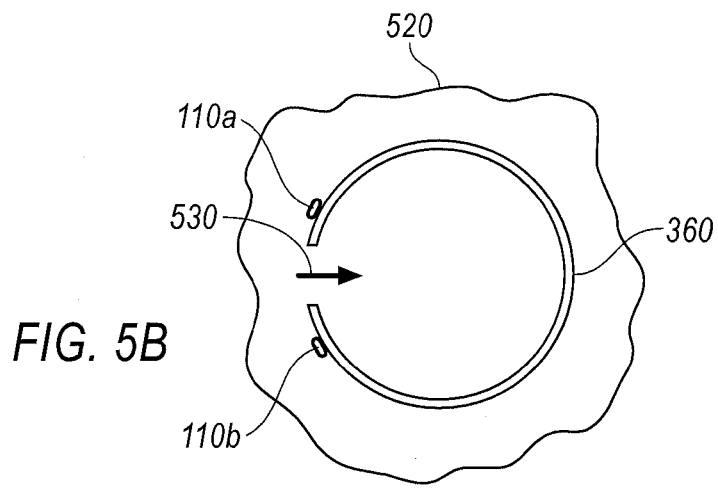
FIG. 5B illustrates a margin test being performed for a particular location.

FIG. 5B shows a margin test being performed for a particular location. Outer cannula 360 is rotatable in order to resect tissue to form the cavity, but is also rotatable to align sensors 110A, 110B to the cavity. Once resection is complete, cavity wall 520 may be tested to determine if the proper margins have been resected to improve the chances that all abnormal tissue has been removed from the patient. User 140 may decide after bulk resection to perform a lavage of the resection cavity using saline and the vacuum system to remove any remaining blood, loose tissue and saline.

Figure 5C:
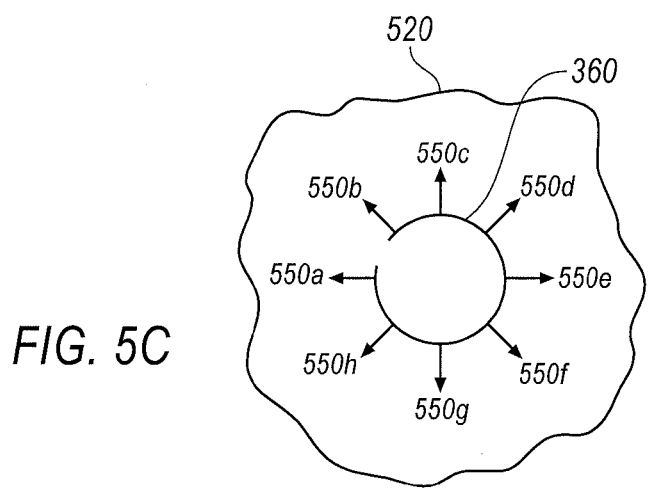
FIG. 5C illustrates a method employing the cannula of FIG. 5A at different orientations with respect to a cavity wall.

At that time, user 140 may employ real-time pathology system 100 to test the margin of cavity wall 520. As shown, user 140 is testing cavity wall 520 at the nine-o-clock position. A vacuum 530 is pulled through outer cannula to locally pull cavity wall 520 against sensors 110A, 110B so that the real-time pathology analysis may be performed. As shown in FIG. 5C, user 140 may employ this method at different orientations with respect to cavity wall 520 in order to fully test the margin for suspicious tissue. For example, FIG. 5C shows rotation of outer cannula 360 (and necessarily sensors 110A, 110B) to perform margin test at locations 550A-550H. The method of rotating outer cannula 360 allows the surgical device to be placed within the patient to analyze the margins by probing the wall of the resected cavity. Moreover, when real-time pathology system 100 is configured for continuous sampling, user 140 may rotate outer cannula 360 to perform a continuous sweep of cavity wall 520, rather than only sampling at particular orientations (e.g., locations 550A-550H).

Figure 6:
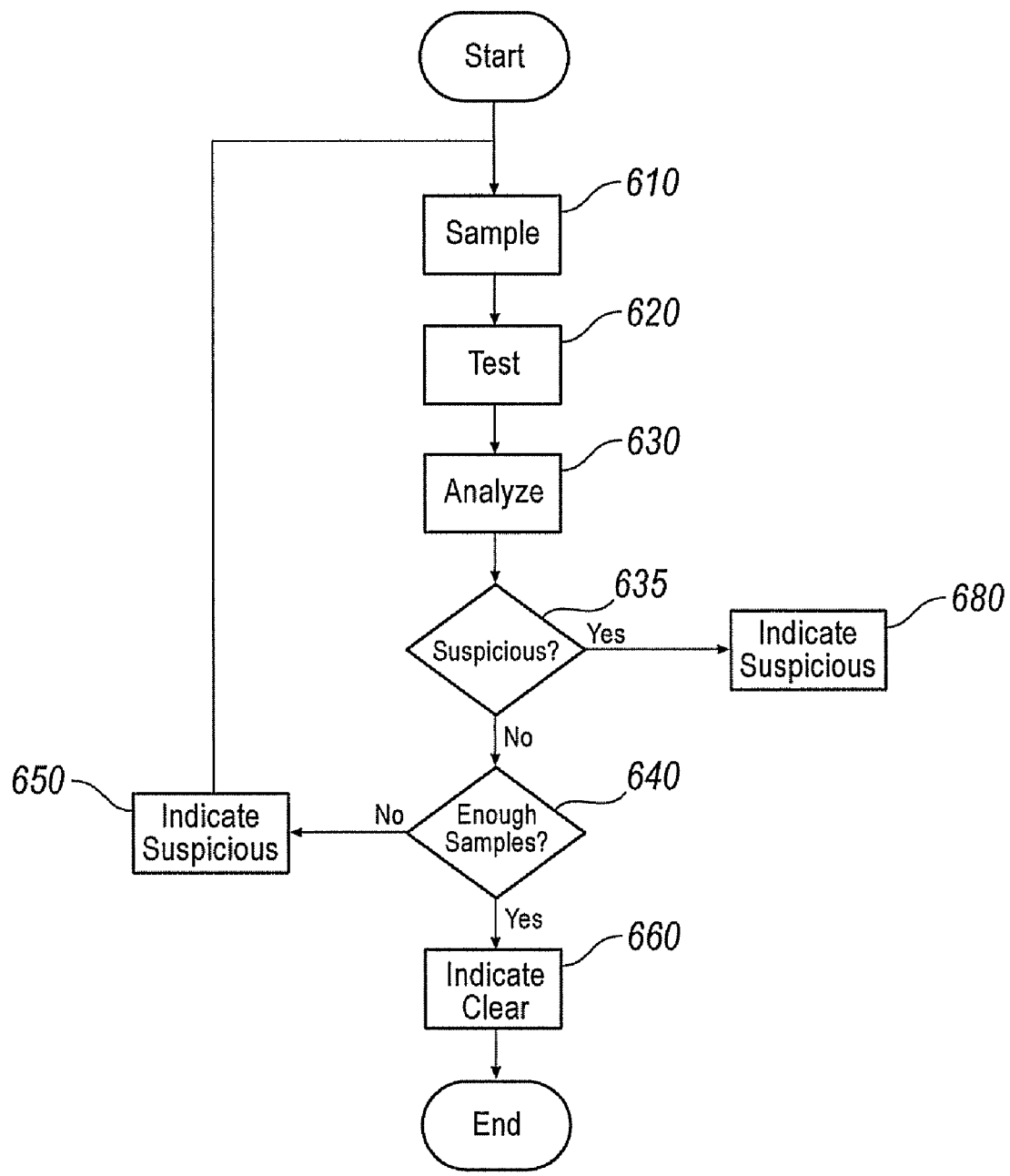
FIG. 6 illustrates a method of real-time pathology margin determination in a cavity after tissue resection.

FIG. 6 shows a method of real-time pathology margin determination in a cavity after tissue resection. The margin determination is typically performed after bulk tissue resection leaves a cavity and it is not known whether all of the abnormal tissue is removed and additional tissue to provide a margin of safety. In step 610, processor 220 commands the surgical device (e.g., resection device 470 of FIG. 4G) to take a sample. When sensor 110 is on the external periphery of, for example, outer cannula 360 the sample may be a real-time measurement from sensor 110. However, a vacuum may be required for this operation in which case processor 220 may command valves to provide the vacuum. Alternatively, where sensor 110 is placed within the fluid path of a resection device (see FIG. 4G) processor 220 may command the resection device to sever a portion of tissue and use a vacuum to transport the resected tissue to sensor 110.

Next, in step 620, processor 220 commands sensor 110 to initiate testing and send information to processor 220. Sensor 110 may activate an illumination source or may release a chemical or biological agent to perform the sensing. Sensor 110 then sends the information to processor 220, typically via signal lines 450A, 450B (see FIG. 4B).

Next, in step 630, processor 220 analyzes the information to determine whether the tissue is suspicious or abnormal. Processor 220 may use threshold analysis, fuzzy logic, statistical methods, etc. to determine whether the sampled tissue is abnormal, as discussed herein.

Next at step 635, processor 220 determines whether the tissue is considered normal or abnormal. If the tissue is abnormal, control proceeds to step 680. If the tissue is not abnormal, control proceeds to step 640.

Next, in step 640, processor 220 determines whether a significant number of samples are taken of the tissue cavity. For example, processor 220 may require at least four positions be tested around the periphery of the resection cavity (see FIG. 5H) before a clear margin indication is provided to user 140. If more samples are needed, control proceeds to step 650. Otherwise, control proceeds to step 660.

Next, in step 650, processor 220 commands user 140 (or, e.g. resection device 470 of FIG. 4G if equipped with a controllable auto-rotation capability) to rotate sensor 110 (via outer cannula 360) within the cavity to a different position (e.g., positions 550A-550H of FIG. 5C). Control then proceeds to step 610 where more tissue is sampled.

Next, in step 660, the process ends with real-time pathology system 100 providing an indication of a clear margin. The user may then remove real-time pathology system 100, provide additional adjuvant treatment, place a surgical site marker, and/or lavage the site before closing. Examples of tissue margins and adjuvant treatments are described in co-pending U.S. patent application Ser. No. 11/550,209, entitled "SYSTEM AND METHOD FOR MINIMALLY INVASIVE DISEASE THERAPY," filed Oct. 17, 2006, the contents of which are included in their entirety herein.

Next, in step 680, when the tissue is considered abnormal a signal is provided to user 140 that the margin is not clean and the process ends. The user may then perform more tissue resection or apply additional treatments.

Figure 7:
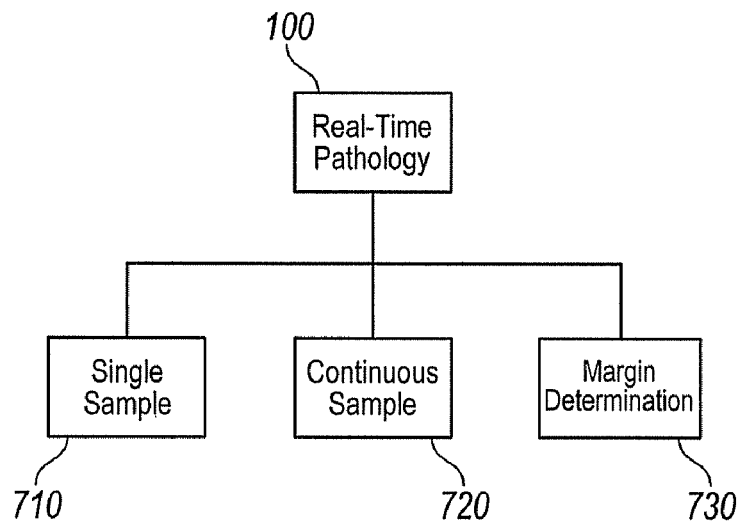
FIG. 7 describes multiple modes of operation for a real-time pathology system.

FIG. 7 describes multiple modes of operation for real-time pathology system 100 including single-sample mode 710, continuous-sampling mode 720, and margin-determination mode 730. Processor 220 may control both real-time pathology system 100 and the surgical device that is used to employ it. For example, during single-sample mode 710 processor 220 may command the surgical device (e.g., resection device 470 of FIG. 4G) to resect a single-sample of tissue. Then, processor 220 may command sensor 110 to send information to processor 220 for analysis. Processor 220 may then command the surgical device to aspirate the resected tissue into a collection canister for further analysis. The sequence may differ from typical use of the surgical device because sensor 110 may require that a vacuum be present that forces the tissue sample against sensor 110 during data acquisition. Alternatively, the control for the surgical device may be abstracted from processor 220 allowing only high-level control of the device. In this case, for example, the surgical device may include the functionality and controls needed to interface with sensor 110 and processor 220.

Continuous sampling mode 720 may be employed when user 140 is initially locating the target region. For example, upon initial visualization of the target regions (e.g., using a surgical site marker) the user may insert a surgical device at the target location. To confirm the location, visualization of the surgical instrument and a surgical site marker may be performed. Secondarily, continuous-sampling mode 720 allows user 140 to further confirm that suspicious regions are being resected. When, for example, user 140 moves surgical instrument away from the target site, the indication of suspicious tissue may not be present. This indicates to user 140 that the lesion may have been completely removed in that area. However, user 140 may wish to resect tissue in other directions until a non-indication of suspicious tissue is continuous. The user may then infer that the lesion has been removed in its entirety.

User 140 may then wish to engage margin-determination mode 730 that provides for a more detailed analysis or an alternative method of analysis. For example, where dyes are used to determine whether the margin is removed, real-time pathology system 100 may expel dye, wait a predetermined time, and then sample the tissue to perform pathology testing.

Figure 8:
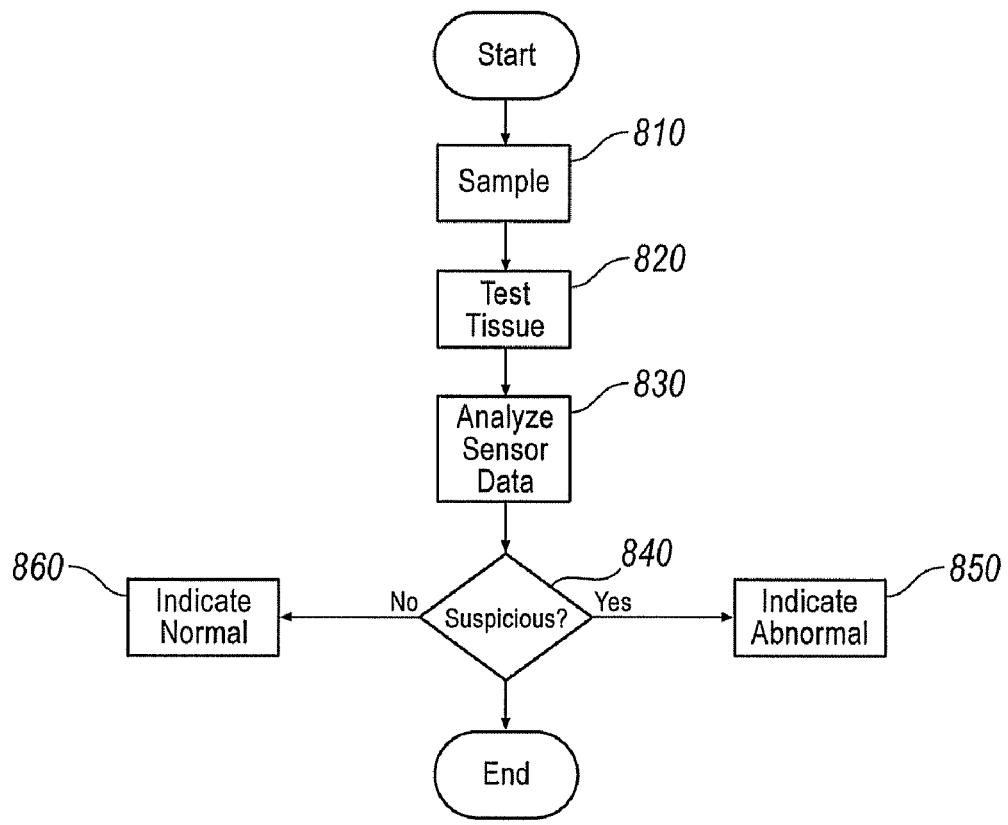
FIG. 8 illustrates a method of real-time pathology determination.

FIG. 8 shows a method of real-time pathology determination 800. In step 810, processor 220 commands the surgical device (e.g., resection device 470 of FIG. 4G) to take a sample. This may be initiated by user 140, or automatically by the surgical device. Typically, the surgical device will pull a vacuum to prolapse tissue through an opening. The surgical device will then move a mechanical cutter to resect the portion of the prolapsed tissue. The surgical device may then use vacuum to transport the resected tissue to sensor 110 (e.g., where sensor 110 is in the fluid path as shown in FIG. 4F). In another example, vacuum may be used to hold the resected tissue against sensor 110 near resection opening.

Next, in step 820, processor 220 commands sensor 110 to test the tissue, gather data and send the data to processor 220. In one example, a one-time chemical marker may be released in proximity to the resected tissue so as to be absorbed by the tissue cells. In another example, miniature probes introduce an electric field for electroporation and then a chemical marker is released. Moreover, sensor 110 then transmits measurement data to processor 220 for analysis.

Next, in step 830, processor 220 performs an analysis of the data sent from sensor 110. In one example, where sensor 110 is an optical sensor, processor 220 evaluates the data to determine whether a frequency is present in light reflected from the tissue. If so, processor 220 may initially determine that the tissue is suspicious and may user further testing to determine the nature of the tissue. For example, where a dye is used that is sensitive to contamination due to the presence of blood, processor 220 may command the surgical device to maintain vacuum and/or to wash the resected tissue with saline to reduce contamination issues. Moreover, processor 220 may require a different analysis be performed to verify the suspicion.

Next, in step 840, processor 220 determines whether the analysis results merit a determination that the tissue is suspicious. For example, the thresholds to determine tissue health may be different for each of single-sample mode 710, continuous-sampling mode 720, and margin-determination mode 730. In single-sample mode 710, processor 220 may command a single determination process that may include a more detailed processing method to improve accuracy. Alternatively, in continuous-sampling mode 720 processor may command a more "rapid" process that may not have the accuracy of single-sample mode 710, but is able to keep pace with numerous tissue resections passing by sensor 110 at a high rate. Alternatively, there may be no differences in accuracy and speed of sampling, and continuous-sampling mode 720 may be more accurate than single-sample mode 710 because more tissue is presented to sensor 110. If the tissue is determined to be abnormal (e.g., the tissue includes indicators or makers of suspicious origins) then control proceeds to step 850. Otherwise, if the tissue is determined to be not-abnormal, control proceeds to step 360.

In step 850, processor 220 indicates to user 140 that the tissue tested is abnormal at outputs 280 (see also FIG. 2). In an example, processor 220 indicates a sound or illuminates a red light to alert user 140 of the presence of possibly cancerous tissue. The process then ends.

In step 860, where processor 220 determines that the tissue is not suspicious, no tone be sounded, a green light may be illuminated, and/or no light may be illuminated. The process then ends.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

With regard to the processes, methods, heuristics, etc. described herein, it should be understood that although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes described herein are provided for illustrating certain embodiments and should in no way be construed to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A system for detecting tissue in a patient comprising:
    a surgical instrument configured for selective insertion into a patient, the surgical instrument further comprising an outer cannula having a tissue sampling aperture positioned adjacent a distal end of the outer cannula;
    an inner cutting cannula positioned within the outer cannula, the inner cutting cannula including a cutting edge selectively moveable across the tissue sampling aperture to sever tissue; and
    a sensor configured to detect at least one property of the tissue of said patient, the sensor fixedly attached to an inner surface of the outer cannula so as to contact tissue prolapsed through the sampling aperture, wherein the inner surface of the outer cannula to which the sensor is attached is oriented axially relative to a longitudinal axis of the outer cannula, and is positioned between the tissue sampling aperture and the distal end of the outer cannula.

2. The system of claim 1, wherein the sensor is positioned opposite the cutting edge of the inner cutting cannula and at a perpendicular distance from a longitudinal axis of the inner cannula not greater than a maximum radial dimension of the inner cannula.

3. The system of claim 1, further comprising an introducer cannula having a proximal opening and a distal opening, wherein the outer cannula is inserted into the introducer cannula prior to selective insertion into a patient.

4. The system of claim 3, wherein the sensor is selectively rotatable relative to the introducer cannula.

5. The system of claim 1, further comprising a vacuum source that delivers vacuum adjacent the sensor.

6. The system of claim 1, wherein the surgical instrument is a tissue resection device.

7. The system of claim 1, wherein the sensor is located adjacent the sampling aperture.

8. The system of claim 1, further comprising a processor electrically communicating with the sensor, the processor analyzing data from the sensor.

9. The system of claim 1, further comprising an indicator.

10. The system of claim 9, wherein the indicator indicates to a user an abnormality of the tissue of the patient.

11. The system of claim 9, wherein the indicator indicates to a user a normality of the tissue of the patient.

12. The system of claim 1, further comprising a tissue collection filter that is configured to retain resected tissue therein, a vacuum source being operatively connected to the tissue collection filter to draw resected tissue into the tissue collection filter.

13. A system for detecting tissue in a patient comprising:
a surgical instrument configured for selective insertion into a patient, the surgical instrument further comprising an outer cannula having a tissue sampling aperture positioned adjacent a distal end of the outer cannula;
an inner cutting cannula positioned within the outer cannula, the inner cutting cannula including a cutting edge selectively moveable across the tissue sampling aperture to sever tissue; and
a sensor configured to detect at least one property of the tissue of said patient, the sensor fixedly attached to an inner surface of the outer cannula so as to contact tissue prolapsed through the sampling aperture, wherein the inner surface of the outer cannula to which the sensor is attached is oriented substantially perpendicular to a longitudinal axis of the inner cutting cannula.

14. The system of claim 13, wherein the sensor and the tissue sampling aperture are generally arranged along a common plane oriented substantially perpendicular to a longitudinal axis of the outer cannula.

15. The system of claim 13, further comprising an introducer cannula having a proximal opening and a distal opening, wherein the outer cannula is inserted into the introducer cannula prior to selective insertion into a patient.

16. The system of claim 15, wherein the sensor is selectively rotatable relative to the introducer cannula.

17. The system of claim 13, further comprising a vacuum source that delivers vacuum adjacent the sensor.

18. The system of claim 13, wherein the surgical instrument is a tissue resection device.

19. The system of claim 13, further comprising a processor electrically communicating with the sensor, the processor analyzing data from the sensor.

20. The system of claim 13, further comprising an indicator.

21. The system of claim 20, wherein the indicator indicates to a user an abnormality of the tissue of the patient.

22. The system of claim 20, wherein the indicator indicates to a user a normality of the tissue of the patient.

23. The system of claim 13, further comprising a tissue collection filter that is configured to retain resected tissue therein, a vacuum source being operatively connected to the tissue collection filter to draw resected tissue into the tissue collection filter.

24. A system for detecting tissue in a patient comprising:
a surgical instrument configured for selective insertion into a patient, the surgical instrument further comprising an outer cannula having a tissue sampling aperture positioned adjacent a distal end of the outer cannula;
an inner cutting cannula positioned within the outer cannula, the inner cutting cannula including a cutting edge selectively moveable across the tissue sampling aperture to sever tissue; and
a sensor configured to detect at least one property of the tissue of said patient, the sensor fixedly attached to an inner surface of the outer cannula so as to contact tissue prolapsed through the sampling aperture, wherein the inner surface of the outer cannula to which the sensor is attached is oriented at an oblique angle relative to a longitudinal axis of the inner cutting cannula.

25. The system of claim 24, wherein the sensor is positioned on an inner surface of the outer cannula that intersects the longitudinal axis of the inner cutting cannula.

26. The system of claim 24, further comprising an introducer cannula having a proximal opening and a distal opening, wherein the outer cannula is inserted into the introducer cannula prior to selective insertion into a patient.

27. The system of claim 26, wherein the sensor is selectively rotatable relative to the introducer cannula.

28. The system of claim 24, further comprising a vacuum source that delivers vacuum adjacent the sensor.

29. The system of claim 24, wherein the surgical instrument is a tissue resection device.

30. The system of claim 24, further comprising a processor electrically communicating with the sensor, the processor analyzing data from the sensor.

31. The system of claim 24, further comprising an indicator.

32. The system of claim 31, wherein the indicator indicates to a user an abnormality of the tissue of the patient.

33. The system of claim 31, wherein the indicator indicates to a user a normality of the tissue of the patient.

34. The system of claim 24, further comprising a tissue collection filter that is configured to retain resected tissue therein, a vacuum source being operatively connected to the tissue collection filter to draw resected tissue into the tissue collection filter.

35. The system of claim 24, wherein the sensor is fixedly attached to the inner cutting cannula for concurrent movement therewith.

36. A system for detecting a characteristic of tissue in a patient comprising:
an outer cannula having a tissue sampling aperture positioned adjacent a distal end of the outer cannula;
an inner cutting cannula positioned within the outer cannula, the inner cutting cannula including a cutting edge selectively moveable across the tissue sampling aperture to sever tissue, and a lumen at least partially defining a fluid path for transporting the severed tissue away from the sampling aperture; and
a sensor configured to detect abnormal tissue of the patient, the sensor positioned within the fluid path and the lumen.

37. The system of claim 36, wherein the inner cutting cannula includes a first end defined by the cutting edge, and an opposite second end, the sensor arranged within the inner cutting cannula between the first end and the second end.

38. The system of claim 36 further comprising a tissue collection filter configured to retain the resected tissue, the filter disposed within the fluid path, wherein the inner cutting cannula includes a first end defined by the cutting edge, and an opposite second end, the sensor being positioned within the fluid path between the first end and the tissue collection filter, and the second end and the tissue collection filter.

39. The system of claim 36, wherein the lumen at least partially defines an inner surface of the inner cutting cannula, the sensor being attached to the inner surface.

40. The system of claim 36, wherein the sensor is fixedly attached to the inner cutting cannula for concurrent movement therewith.

41. The system of claim 36, further comprising a processor electrically communicating with the sensor, said processor analyzing data from the sensor.

42. The system of claim 36, further comprising an indicator related to a determination of abnormality of the tissue.

* * * * *